United States Patent [19]

Schlosberg et al.

[11] 4,277,327

[45] Jul. 7, 1981

[54] TREATMENT OF PHENOL-CONTAINING FEED STREAMS

[75] Inventors: Richard H. Schlosberg, New Providence; Martin L. Gorbaty, Westfield, both of N.J.

[73] Assignee: Exxon Research & Engineering Co., Florham Park, N.J.

[21] Appl. No.: 95,642

[22] Filed: Nov. 19, 1979

[51] Int. Cl.$^3$ .................... C10G 19/08; C07C 41/00
[52] U.S. Cl. .................... 208/263; 208/8 R; 208/48 R; 568/630
[58] Field of Search .............. 208/263, 8 R, 48 R; 568/630, 749, 761, 762

[56] References Cited

U.S. PATENT DOCUMENTS

| | | | |
|---|---|---|---|
| 1,801,901 | 4/1931 | Britton et al. | 568/630 |
| 1,819,687 | 8/1931 | Miller | 568/761 |
| 3,617,513 | 11/1971 | Wilson et al. | 208/127 |
| 3,671,422 | 6/1972 | Morrow | 208/79 |
| 3,928,171 | 12/1975 | Yan et al. | 208/18 X |

FOREIGN PATENT DOCUMENTS

| | | | |
|---|---|---|---|
| 866064 | 8/1978 | Belgium | 208/263 |
| 838900 | 3/1939 | France | 208/263 |
| 494450 | 10/1938 | United Kingdom | 208/263 |

OTHER PUBLICATIONS

Gardner et al., "Magnesium Hydroxide in Petroleum Industry", Ind. Eng. Chem. 24, 1141–1146 (1932).
Blom et al., Fuel 36, 135–153 (1957).
Yohe et al., J. Am. Chem. Soc. 69, 2644–2648 (1947).

*Primary Examiner*—Delbert E. Gantz
*Assistant Examiner*—G. E. Schmitkons
*Attorney, Agent, or Firm*—Henry E. Naylor

[57] ABSTRACT

Phenol-containing streams are treated by an oxygen-alkylation process to convert substantially all of the phenol groups to ether groups. The oxygen-alkylation process comprises contacting the phenol-containing stream, preferably a coal liquid, with (a) a basic solution comprising one or more oxides or hydroxides of a metal selected from the group consisting of alkali and alkaline-earth metals; and (b) an alkylating agent represented by the formula RX where R is a $C_1$ to $C_{18}$ alkyl, allyl, cycloalkyl, haloalkyl, benzyl or arylalkyl group provided X is located on the alkyl portion of the compound and X is sulfate or a halide selected from the group consisting of chlorine, bromine and iodine.

13 Claims, No Drawings

TREATMENT OF PHENOL-CONTAINING FEED STREAMS

BACKGROUND OF THE INVENTION

1. Field of the Invention

The present invention relates to improving the properties of phenol-containing streams, such as coal liquids and petroleum asphaltenes, by oxygen-alkylation. The resulting upgraded stream has improved storage and processing properties.

2. Description of the Prior Art

The viscosity of phenol-containing hydrocarbonaceous streams such as coal liquids and petroleum asphaltenes generally increases with time, thereby presenting stability problems in the storage and use of such liquids. Many of these liquids are rich in heteroatoms, and especially organic oxygen such as phenolic and carboxylic oxygen. It is believed that increases in molecular weight and consequently in viscosities are brought about in two ways: (1) by hydrogen bond formation and (2) by free radical initiated polymerization. The instability of streams is evidenced by increasing color intensity with time—mainly owing to the presence of phenols.

Furthermore, because streams such as coal liquids are generally rich in phenolic and carboxylic functionality, they are highly polar and not compatible with less polar petroleum liquids of comparable boiling point range. Thus, segregation occurs because the petroleum liquids, which lack highly polar groups, cannot participate in the intermolecular association between adjacent coal liquid molecules.

Although various attempts have been proposed to eliminate or at least alleviate the aforementioned problems, there is still a need in art to develop more efficient and economical ways of achieving stability in such liquids.

SUMMARY OF THE INVENTION

In accordance with the present invention, phenol-containing streams are treated by an oxygen-alkylation process (hereinafter sometimes referred to as O-alkylation) in order to convert substantially all of the phenol groups to ether groups.

The O-alkylation process of the present invention comprises contacting the phenol-containing stream, preferably a coal liquid, with (a) a basic solution comprising one or more oxides or hydroxides of a metal selected from the group consisting of alkali and alkaline-earth metals wherein the metal oxide and/or hydroxide is capable of removing the acidic protons of the phenolic groups; and (b) one or more alkylating agents represented by the formula: RX where R is a $C_1$ to about $C_{18}$, preferably a $C_1$ to $C_4$ group selected from the group consisting of alkyl, allyl, cycloalkyl, haloalkyl, benzyl and arylalkyl provided X is located on the alkyl portion of the compound and X is sulfate or a halide selected from the group consisting of chlorine, bromine and iodine.

In a preferred embodiment of the present invention, a coal liquid is first contacted with an alkali or alkaline-earth metal oxide or hydroxide solution capable of removing the acidic protons from the phenolic and carboxylic groups of the coal liquid and forming a phenate salt of the alkali or alkaline-earth metal. The resulting upgraded coal liquid is separated from the aqueous phase (containing the salt) wherein the aqueous phase is treated with the alkylating agent to produce ether groups, and if applicable, ester groups.

DETAILED DESCRIPTION OF THE INVENTION

Phenol-containing streams which can be treated according to the present invention are those streams soluble enough in an aqueous base solution to allow the base to react with the phenolic and/or carboxylic groups of the stream. For example, if the phenol-containing stream is a hydrocarbonaceous stream such as a coal liquid fraction or petroleum fraction, only those fractions having a boiling point less than about 370° C., preferably less than about 250° C., are suitable for treatment herein.

By coal liquid we mean any coal liquid containing phenol groups regardless of derivation. Non-limiting examples of processes suitable for producing coal liquids which can be treated according to the present invention include hydrogenation, hydrogen donor solvent reactions, pyrolysis in the presence or absence of hydrogen, and extraction including supercritical extraction in various solvents.

Although not wishing to be limited hereby, one preferred method for obtaining coal-liquid is the Exxon Donor Solvent (EDS) process for the liquefaction of coal and described in U.S. Pat. No. 3,617,513 incorporated herein by reference. Briefly stated, the EDS process involves the formation of a slurry of coal in a hydrogen-donor solvent, such as tetralin, maintained at elevated temperatures of about 260° C. to 370° C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperatures above about 370° C. under a pressure effective to maintain the dispersed slurry substantially in liquid phase, generally about 350 p.s.i.g. to 3500 p.s.i.g. In this second temperature stage, the dissolved coal particles are well dispersed in the hydrogen-donor solvent and the change of a hydrogen-donor stabilization of free radicals generated by bond breaking it maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contains phenols, is then distilled and hydrogenated, the gases drawn off, and the bottoms removed for coking and gasification.

Although it is not necessary from a technical point of view that the stream be rich in phenols, it is desirable to apply the present invention in those circumstances where enough phenols are present to cause a stability or compatibility problem which can be economically overcome by use of this invention. It will be noted that phenol-containing streams other than hydrocarbonaceous streams can be treated according to the present invention. For example, waste water streams containing phenols resulting from various chemical and petroleum processes can also be treated so that the phenols are converted to an ether-rich hydrocarbon phase in said waster water stream and separated by conventional separation methods.

The term "petroleum asphaltenes" means those higher boiling fractions and residua found in crude petroleum and its distillates which are generally highly polar and insoluble in common paraffic solvents.

Base solutions suitable for use herein are those aqueous solutions comprised of one or more alkali or alkaline-earth metal oxides or hydroxides which are capable of removing the proton from the phenolic or carboxylic groups and forming the corresponding metal phenate salt. Preferred are the oxides and hydroxides of the alkali metals as well as calcium and barium and mixtures thereof. More preferred are the hydroxides of sodium, potassium, calcium and barium and mixtures thereof.

The basic solution must be present in at least stoichiometric quantities relative to the number of phenolic and if applicable, carboxylic sites contained in the stream. Preferably an excess amount of base solution is used, for example two or more times the stoichiometric amount, in order to drive the reactions to completion. The precise concentration of base solution can easily be determined by one having ordinary skill in the art and will not be discussed in further detail.

The term phenol-containing as used herein means a stream containing the class of phenol compounds in which one or more hydroxy groups are attached to an aromatic ring and where the aromatic ring may also contain a heteroatom. Non-limiting examples of such compounds include phenol itself (also known as benzophenol), the cresols, xylenols, recorcinol, naphthols, 8-hydroxyquinoline and 4-hydroxyquinoline.

Non-limiting examples of phenol-containing hydrocarbonaceous streams which can be treated according to the present invention include such streams as those resulting from the processing of coal and petroleum, and those existing as impurities in such streams as linear paraffins etc.

The alkylating agent suitable for use herein can be comprised of one or more compounds represented by the formula: RX, where R is a $C_1$ to about $C_{18}$, preferably a $C_1$ to $C_4$ group selected from the group consisting of alkyl, allyl, cycloalkyl, haloalkyl, benzyl and arylalkyl provided X is located on the alkyl portion of the group and X is a leaving group such as sulfate or a halide selected from the group consisting of chlorine, bromine and iodine. Preferably X is chlorine and the haloalkyl is preferably a $C_1$ to $C_4$ chloroalkyl. The carbon atom to which X is attached must be a primary or secondary carbon, more preferably a primary carbon.

It will be noted that the alkylating agent can be prepared from its hydrocarbon precursor, for example, by free radical halogenation of alkenes or halogenation of hydrocarbon streams such as $C_1$ to $C_4$ gas streams obtained independently or as a result of petroleum or coal processing. The alkylating agent may also be prepared by the addition of sulfuric acid to olefins.

In general, the phenol-containing feed stream is contacted with both the base solution and the alkylating agent at a temperature from about ambient temperature (20° C.) to about 100° C., preferably from about ambient temperature to about 50° C., for a period of time sufficient to allow complete oxygen-alkylation. This period of time is, of course, dependent on such factors as the temperature of the phenol-containing feed stream, the reactive nature of the oxide and/or hydroxide, and the reactive nature of the alkylating agent. This period of time can be determined by routine experimentation by one having ordinary skill in the art.

The oxygen-alkylation of the phenol-containing stream can be accomplished in either one stage or in multiple stages. For example, in a one-stage process all of the ingredients are mixed together and the resulting oxygen-alkylated component enters the organic phase or forms a separate organic phase when the phenol-containing stream is not a hydrocarbonaceous stream. When the phenol-containing stream is a hydrocarbonaceous stream such as a coal liquid or petroleum asphaltene, it may be desirable to perform the O-alkylation in two or more stages in order to acquire a concentrated product stream of high quality ethers along with the upgraded hydrocarbonaceous stream. That is, the hydrocarbonaceous stream can first be contacted with the base solution at temperatures less than about 100° C., thereby providing an organic phase comprised of the upgraded coal liquid and an aqueous phase containing a phenate salt of the respective metal base. The two phases are separated and the aqueous phase containing the salt is treated with the alkylating agent at temperatures less than 100° C., thereby providing a two phase system comprised of (a) an aqueous phase containing the metal halide or sulfate formed from the cation of the base and the anion of the alkylating agent, and (b) an organic phase comprised mainly of ethers.

Coal liquids obtained from any coal are suitable for treatment by the present invention so long as phenolic groups are present. Non-limiting examples of some such coals include bituminous, subbituminous, and lignite. Typically, the aforementioned coals have the following character: carbon content raging from about 55 to 88 wt. %, hydrogen content ranging from about 3.8 to 6.2 wt. %, and oxygen content ranging from about 2.6 to 33 wt. % (DAF or Dry Ash Free Basis) and a hydrogen to carbon (H/C) ratio of about 0.7 to 1.1.

Infrared analysis may be used to demonstrate that the phenol groups have been converted to ethers. If the added hydrocarbon group is IR-active, then the appearance of the appropriate infrared frequency is observed. Other wellknown analytical methods may also be employed if desired. The ultimate analysis of percent C, H, N, S and O is altered in a fashion which is consistent with the expected change owing to the added hydrocarbon substituent.

The following examples serve to more fully describe the manner of making and using the above-described invention, as well as to set forth the best modes contemplated for carrying out various aspects of the inventions. It is understood that these examples in no way serve to limit the true scope of this invention, but rather are presented for illustrative purposes.

EXAMPLE 1

60.7 grams of Wyodak coal (10/20 mesh, dry) was heated under a nitrogen sweep from about 25° C. to 500° C. over a period of one hour, then pyrolyzed between 500° C. and 520° C. for 0.5 hours. (This treatment is similar to the well known Fischer-Assay Pyrolysis). After pyrolysis, a char weighing 42.16 g (69 wt. %) remained thereby indicating the formation of 31 wt. % volatiles. The volaties were comprised of from 10 to 12 wt. % gaseous constituent, 10 to 12 wt. % hydrocarbonaceous liquid (organic constituent) and the remainder water. Of the organic constituent about 30 wt. % was phenolic.

The volatiles were passed through a cold trap containing 10 ml water and 20 ml of a 50% sodium hydroxide solution. The resulting aqueous/organic material was stirred with 20 ml (45.6 g; 0.32 mol) of methyl iodide at 25° C. for 168 hours and the organic material recovered in ether.

The volatiles, immediately after pyrolysis and before passing through the cold trap for alkylation, were compared by gas chromatography with the organic material recovered in ether. The organic material, recovered in ether, indicated the presence of anisoles and the absence of phenols, wherein the coal liquid or volatiles formed immediately after pyrolysis but before O-alkylation showed the presence of phenols and the absence of compounds such as anisoles.

This example shows that phenols, in phenol-containing streams such as coal liquids, can be converted to ethers by the alkylation method of this invention.

EXAMPLE 2

The pyrolysis procedure of Example 1 above was followed except 44.1 g of Wyodak coal was used. After pyrolysis, a char weighing 29.55 g (67 wt. %) remained leaving 33 wt. % volatiles which were passed through a cold trap containing 10 g of 50% sodium hydroxide solution and 35 ml of water. The resulting aqueous/organic material was stirred for 168 hours at 25° C. with 20 ml (26.3 g; 0.21 mol) of 2-bromopropane. The resultant organic product was recovered in $CDCl_3$ and analyzed by nuclear magnetic resonance which indicated the presence of —O—C—H groups at 3.8–4.6 δ.

Nuclear magnetic resonance was used to analyze the product of this example instead of gas chromatography because an authentic model sample for comparison on the gas chromatograph was unavailable. This resonance at 3.8–4.6 δ shows that the phenols of the coal liquid were converted to ethers in the $CDCl_3$ solution.

EXAMPLE 3

25 ml (20 g) of a coal liquid naphtha cut containing about 10 wt. % phenols and derived from Illinois #6 coal by the Exxon Donor Solvent Coal Liquefaction Process was stirred for 2 hours at room temperature with 6 ml of water and 4 ml of a 50% sodium hydroxide solution. 5 g of methyl iodide (oxygen-alkylating agent) was added and stirred for 168 hours at room temperature resulting in two phases, an organic phase weighing 16.9 g and an aqueous phase weighing 13.5 g.

The naphtha before O-alkylation and after O-alkylation was analyzed for phenols by gas chromatography. The results are set forth in Table I below.

TABLE I

| R.T.[1] (min) | Wt. %[2] Compound in Untreated Naphtha | Wt. %[2] Compound in Treated Naphtha | Compound |
|---|---|---|---|
| 12.8 | 8.8 | 0 | phenol |
| 14.0 | 2.0 | 0 | cresols |
| 14.6 | 3.5 | 0 | cresols |
| 9.4 | 0 | 0.6 | anisole |

1 = retention time in gas chromatograph (GC)
2 = based on total weight of naphtha cut The above table shows that by the process of the present invention phenols are converted to ether in such phenol-containing streams as coal liquids. For example, after injecting a sample of raw naphtha into a chromatograph, phenol compounds came off at specific retention times. Phenol came off at a retention time of 12.8 minutes at such concentrations that indicated that 8.8 wt. % of the naphtha contained phenol. Other phenol compounds such as cresols came off at 14.0 and 14.6 minutes retention time. After oxygen-alkylation the naphtha indicated the absence of phenol compounds when measured by gas chromatography.

Color stability is markedly affected by oxygenalkylation. For example, the relative absorptivities at 490 nm of the starting naphtha (at t=168 hrs) versus the naphtha after oxygen-alkylation (at t=168 hrs) was 3.8 to 1 or a 74% reduction in color intensity after oxygen-alkylation. As previously mentioned, instability of a phenol-containing stream such as coal liquid may be evidenced by an increase in color intensity of the liquid over time.

EXAMPLE 4

Example 3 above was repeated except after sodium hydroxide treatment the solution was stirred with 3.5 g of 2-bromopane for 168 hours at room temperature. A color reduction of 78% was measured in the solution after 168 hours evidencing the conversion of phenols to ethers.

EXAMPLE 5

Ten grams of a coal liquid naphtha derived from Illinois #6 coal and liquefied by the Exxon Donor Solvent Process and having a phenol content of about 10 wt. % was stirred at 25° C. for 1.5 hours with 5 grams of a 10% sodium hydroxide solution. Two layers, an organic layer and an aqueous layer, resulted. The layers were separated and the organic layer (which is the coal liquid after oxygenalkylation) showed no measurable signs of —O—H (phenols) stretch when analyzed by infrared spectroscopy. The aqueous layer was treated with 1 gram of dimethyl sulfate at room temperature for one hour, thereby forming an organic product in the aqueous layer. This product was extracted with methylene chloride and after analysis by infrared spectroscopy showed no —O—H (phenols) functionality. This methylene chloride composition was then analyzed by gas chromatography which indicated the presence of only the following, excluding methylene chloride itself: Anisole

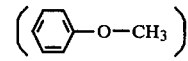

and the following methyl Anisoles:

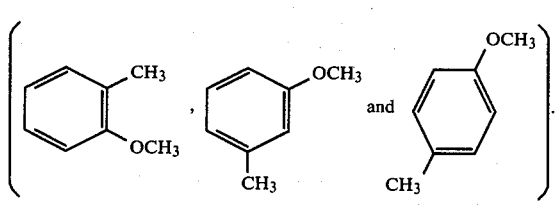

This Example shows that phenols of phenol-containing streams such as coal liquids can be separated from the stream and converted to ether-rich side streams by practice of the present invention. These ether rich side streams can then be used as high octane blending agents for gasoline.

What is claimed is:

1. A process for improving the properties of coal liquids by oxygen-alkylation comprising contacting the coal liquid at a temperature less than about 100° C. with:

(a) an aqueous base solution comprised of an alkali or alkaline-earth metal oxide or hydroxide or mixtures thereof, wherein the base solution is capable of removing the acidic protons of the phenolic and carboxylic functionality of the coal liquid and forming the corresponding metal phenate salt; and (b) one or more alkylating agents represented by the formula RX where R is a $C_1$ to about $C_{18}$ group selected from the group consisting of alkyl, allyl, cycloalkyl, haloalkyl, benzyl and arylalkyl, provided X is located on the alkyl portion of the alkylating agent and X is sulfate or a halide selected from the group consisting of chlorine, bromine and iodine.

2. The process of claim 1 wherein the base solution is a hydroxide selected from the group consisting of alkali metals, calcium and barium.

3. The process of claim 1 wherein the alkylating agent is a $C_1$ to $C_4$ alkyl sulfate or alkyl halide.

4. The process of claim 3 wherein the alkylating agent is selected from the group consisting of methyl chloride, methyl iodide, and dimethyl sulfate.

5. The process of claim 4 wherein the base solution is a hydroxide selected from the group consisting of alkali metals, calcium and barium.

6. The process of claim 1 wherein at least twice the stoichiometric amount of base to phenolic content of the coal liquid is employed.

7. A process for improving the properties of a phenol-containing stream by oxygen-alkylation comprising contacting the stream at a temperature less than about 100° C. with:

(a) an aqueous base solution comprised of an alkali or alkaline-earth metal oxide or hydroxide or mixtures thereof, wherein the base solution is capable of removing the acidic protons of the phenolic and carboxylic functionality of the stream and forming the corresponding metal phenate salt; and (b) one or more alkylating agents represented by the formula RX where R is a $C_1$ to about $C_{18}$ group selected from the group consisting of alkyl, allyl, cycloalkyl, haloalkyl, benzyl and arylalkyl, provided X is located on the alkyl portion of the alkylating agent and X is a sulfate or a halide selected from the group consisting of chlorine, bromine and iodine.

8. The process of claim 7 wherein the base solution is a hydroxide selected from the group consisting of alkali metals, calcium and barium.

9. The process of claim 7 wherein the alkylating agent is a $C_1$ to $C_4$ alkyl sulfate or alkyl halide.

10. The process of claim 9 wherein the alkylating agent is selected from the group consisting of methyl chloride, methyl iodide and dimethyl sulfate.

11. The process of claim 10 wherein the base solution is a hydroxide selected from the group consisting of alkali metals, calcium and barium.

12. The process of claim 7 wherein at least twice the stoichiometric amount of base to phenolic content of the stream is employed.

13. The process of claim 7 wherein the phenol-containing stream is a waste-water stream.

* * * * *